US011350882B2

United States Patent
Baag et al.

(10) Patent No.: US 11,350,882 B2
(45) Date of Patent: Jun. 7, 2022

(54) ARRANGEMENT FOR DELAYED ELECTRICAL CHARGE EQUALIZATION DURING ADMINISTRATION OF STIMULATION CURRENT PULSES AND MEASUREMENT OF ELECTRICAL REACTIONS EVOKED BY THE PULSES

(71) Applicant: inomed Medizintechnik GmbH, Emmendingen (DE)

(72) Inventors: Matthias Baag, Blankenfelde (DE); Hanno Gao, Heidelberg (DE); Michael Tomilov, Freiburg i. Br. (DE)

(73) Assignee: inomed Medizintechnik GmbH, Emmendingen (DE)

( * ) Notice: Subject to any disclaimer, the term of this patent is extended or adjusted under 35 U.S.C. 154(b) by 84 days.

(21) Appl. No.: 16/431,045

(22) Filed: Jun. 4, 2019

(65) Prior Publication Data
US 2020/0029910 A1    Jan. 30, 2020

(30) Foreign Application Priority Data

Jul. 25, 2018 (DE) .......................... 102018118019.5

(51) Int. Cl.
*A61B 5/00* (2006.01)
*A61N 1/36* (2006.01)
(Continued)

(52) U.S. Cl.
CPC .............. *A61B 5/7217* (2013.01); *A61B 5/24* (2021.01); *A61N 1/36125* (2013.01); *A61N 1/36157* (2013.01); *H03K 17/6871* (2013.01)

(58) Field of Classification Search
CPC ............ A61N 1/36125; A61N 1/36135; A61N 1/36157; A61N 1/3912; A61B 5/7217; A61B 5/7228; A61B 5/04001; A61B 5/04
See application file for complete search history.

(56) References Cited

U.S. PATENT DOCUMENTS 4,987,902 A * 1/1991 Couche ................. A61B 5/301
600/509
8,755,904 B2 6/2014 Baag
(Continued)

FOREIGN PATENT DOCUMENTS

| DE | 102013010893 | 1/2014 |
| WO | 02082982 | 10/2002 |
| WO | 2016057244 | 4/2016 |

OTHER PUBLICATIONS

Merrill, Daniel R., et al., "Electrical stimulation of excitable tissue: design of efficacious and safe protocols", Journal of Neuroscience Methods 141, pp. 171-198, 2005.

*Primary Examiner* — Carl H Layno
*Assistant Examiner* — Aya Ziad Bakkar
(74) *Attorney, Agent, or Firm* — Volpe Koenig (57) ABSTRACT

An arrangement for electrical charge equalization after generation of stimulation current pulse(s), containing a bridge circuit, switching elements, a bridge branch between two legs of the bridge circuit, into which a load resistance is introducible, and a power source for generating a stimulation current pulse, connected to the legs of the bridge circuit that enables an electrical current via one leg through the bridge branch and through a leg connected to the other end of the bridge branch with corresponding switch position. A capacitive element is in the bridge branch for generating a current for electrical charge equalization for current introduced by stimulation current pulse(s) and is configured such that, between one or more stimulation current pulses and a discharge of the capacitive element via stimulation electrode (s), a delay time window is maintained, which is used for measuring electrical physiological signals induced as a reaction to the stimulation current pulse(s).

14 Claims, 7 Drawing Sheets (51) Int. Cl.
*A61B 5/24* (2021.01)
*H03K 17/687* (2006.01)

(56) References Cited

U.S. PATENT DOCUMENTS

| | | | |
|---|---|---|---|
| 9,107,585 | B1 | 8/2015 | Wong et al. |
| 2005/0107834 | A1* | 5/2005 | Freeman ............... A61N 1/3912 |
| | | | 607/5 |
| 2014/0134075 | A1 | 5/2014 | Fukouka et al. |
| 2015/0223710 | A1 | 8/2015 | Cong et al. |
| 2016/0310741 | A1 | 10/2016 | Baru et al. |
| 2017/0072196 | A1* | 3/2017 | Ridler ................ A61N 1/36038 |
| 2017/0095667 | A1* | 4/2017 | Yakovlev ............. A61N 1/0553 |
| 2017/0147064 | A1 | 5/2017 | Yang et al. |
| 2017/0157413 | A1* | 7/2017 | Anderson et al. . A61N 1/39622 |
| 2018/0169426 | A1* | 6/2018 | Montague .............. G16H 80/00 |

* cited by examiner

ARRANGEMENT FOR DELAYED ELECTRICAL CHARGE EQUALIZATION DURING ADMINISTRATION OF STIMULATION CURRENT PULSES AND MEASUREMENT OF ELECTRICAL REACTIONS EVOKED BY THE PULSES

INCORPORATION BY REFERENCE

The following documents are incorporated herein by reference as if fully set forth: German Patent Application No. 102018118019.5, filed Jul. 25, 2018.

BACKGROUND

The invention relates to an arrangement, configured for electrical charge equalization upon the generation of one or more stimulation current pulses, preferably during an operation or furthermore for other diagnostic purposes, containing a bridge circuit, switching elements, a bridge branch between two legs of the bridge circuit, into which a load resistance can be introduced, and at least one power source for generating at least one stimulation current pulse, which is connected to the legs of the bridge circuit in such a way that it enables an electrical current via a leg through the bridge branch and furthermore through a leg connected to the other end of the bridge branch with corresponding switch position.

Figure 1:
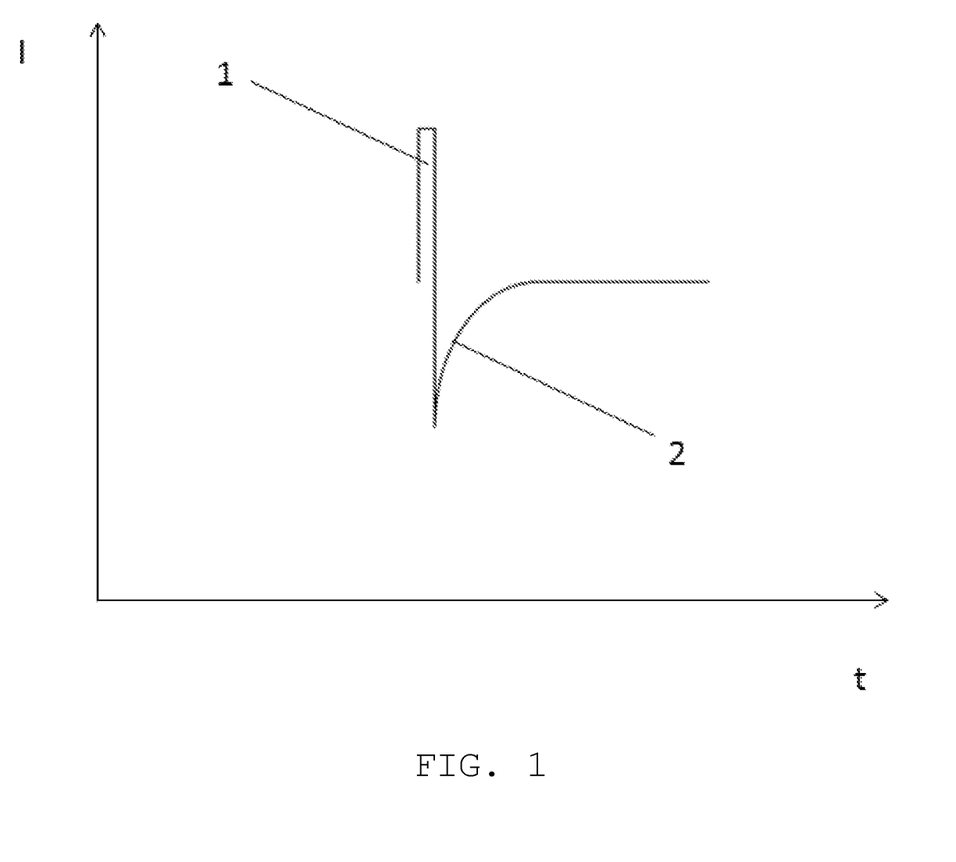
FIG. 1 shows the current curve of a monopolar stimulation current pulse with direct charge equalization without delay (as to be expected from the conceivable prior art according to DE 2013 0101893 A1).

DE 10 2013 010893 A1 describes an arrangement mentioned at the outset for generating at least two different stimulation currents of preferably opposing polarization having four legs, in which during the application a patient, a body part of a patient, patient tissue, or a patient organ is interconnected as a load resistance, for producing stimulation currents for intraoperative stimulation. FIG. 1 therein shows a load resistance (for example, a body part of a patient, such as his head). It is located in the bridge branch 7. The switching elements S1 and S2 and the power sources having switching element IS1 and IS2 may be opened and closed arbitrarily. The H-bridge thus enables the advantage of a biphasic constant power source (for example, for stimulation) upon use of a nonsymmetrical supply voltage, since the two terminals (polarization) of the load can be exchanged simply and very rapidly by the switching of the switching elements.

Such a circuit is mentioned incidentally in DE 10 2013 010893, in which a capacitor in the bridge branch can be connected in series to the load resistance, which capacitor is charged during a current flow through this branch. The charge which has been built up during the current flow could be dissipated again directly thereafter on such a basis—as shown in FIG. 1 as prior art of the disclosure of the present invention.

FIG. 1 shows (as a conceivable, but not described variant according to DE 2013 0101893 A1) an idealized schematic depiction of the resulting current curve during a stimulation using a stimulation current pulses having subsequent direct passive capacitance discharge curve.

In electrical circuits for stimulation in a medical device, in particular in unipolar electrical stimulation, the risk of electrolysis exists, inter alia. Electrolysis is prevented by a DC (direct current) polarization equalization taking place directly following the stimulation. U.S. Pat. No. 4,373,531 attempts to reduce the negative effect by a part of the discharge already taking place before the actual stimulus during an active discharge. Other common methods use a suppression of the measurement artifacts by subtraction of an artifact template from the response signal (WO 2016/057244), special waveforms for minimizing artifacts (U.S. Pat. No. 9,107,585), so-called "blanking" (no measurement, for example, during the discharge. For example, in the therapeutic application in pacemakers, inter alia, for example, US 2015/223710 A1 or US 2017/147064 A1). US 2014/134075 does mention delays between pulses for charge balancing in implants, but not for reducing artifacts in the measured signal. WO 02/082982 A1 uses a pulse scheme to reduce electrical artifacts during the measurement of neuronal reactions in cochlear implants, in which after a stimulus allocated into a first phase having a stimulus of a first polarization and a second phase having a stimulus of opposing polarization, a further compensatory stimulus is administered to remedy residual charge with action against a stimulus artifact which is based on the charging of the tissue during the stimulation.

D. R. Merril et al., J. Neurosci. Meth. 141, 2015, 171-198, describes general damaging effects such as electrode corrosion, etc., and the possible remedying thereof by counter charges, possibly with delay between stimulation phase and countercurrent to avoid the suppression of action potentials.

It has been possible to establish that under physiological conditions, a charge equalization has a negative effect on the detection of evoked potentials caused by the stimulation. If the electrophysiological response to a neurostimulation is detected by signaling with the aid of a measuring modality, then the electrophysiological reactions (the evoked potential), in particular responses occurring immediately after the stimulation, are overlaid by the charge equalization (the discharge curve of a coupling capacitor), measurement artifacts result.

SUMMARY

Against this background, the object of the invention is to provide novel devices and methods for electrical stimulation during operations or for other diagnostic purposes on patients, which enable counter currents to the stimulation current (administered as stimulation current pulse(s)) to reduce or avoid electrolytic effects to be provided and, on the other hand, to enable a measurement of physiological electrical signals induced by stimulation current without measurement artifacts.

This is achieved according to the invention in a surprisingly simple manner by an arrangement mentioned at the outset being characterized in that it contains (connected in series), in the bridge branch with the load resistance, a capacitive element for generating a current for electrical charge equalization for current introduced by one or more stimulation current pulses and is configured in such a way that a delay time window is maintained between one or more stimulation current pulses and a discharge of the capacitive element via one or more stimulation electrodes. The delay time window is available for the interference-free measurement of electrical physiological signals induced as a reaction to the stimulation current pulse or pulses (neurophysiological response) and is used for this purpose. This means a measurement takes place in particular in the time window which is not directly influenced by the stimulation current pulse or pulses and the discharge of the capacitance.

The invention is advantageous in particular anywhere where the location of the electrical stimulation and the location of the derivation are very close to one another. Especially in these cases, the neurophysiological response is to be expected shortly after triggering the stimulation and is therefore frequently overlaid by one or more stimulation artifacts. The artifact can frequently be substantially greater in its amplitude in this case than the response to be expected. Due to the delay during at least part of the stimulation artifact by means of the invention, the response potential is measurable in uninfluenced or hardly influenced form and can thus be made visible and analyzed.

The general terms above and hereafter are in particular defined by the more specialized meanings described hereafter, wherein one, more, or all more general terms can be replaced by more specialized meanings, which results in preferred variants (embodiments) of the invention.

"Arrangements" means device systems or devices which are configured for the purposes mentioned above and hereafter, i.e., include means required for the purposes, which is ensured by corresponding hardware (in particular as described in detail herein) and corresponding (above all computer-implemented) software.

Electrical charge discharge after the generation of one or more stimulation currents is to be understood in particular to mean that the total of the charges administered in the stimulation currents at the stimulation electrode or electrodes are compensated for again (at least substantially) by the discharge of the capacitive element.

The arrangements according to the invention can be used, for example, during an operation (intraoperative, wherein, for example, it is possible to monitor the integrity of nerve paths, which could be damaged during an operation) or furthermore for other diagnostic purposes, in general for "neuromonitoring".

Examples (which are not to restrict the scope of the invention and merely relate to preferred embodiments of the invention) for corresponding applications are the D-wave, somatosensory evoked potentials (SEP), for example, of the trigeminus, and corticobulbar motor evoked potentials.

The D-wave represents the direct response of the spinal cord to an electrical stimulation. In clinical routine, this stimulation corresponds to the transcranial (occurring through the cranium) electrical stimulation of the motor cortex to trigger a corresponding motor response in the periphery. The D-wave can then be derived directly on the spinal cord using special electrodes (D-wave catheter). Due to the additional derivation of the D-wave with respect to the motor evoked potentials directly from the muscles, a detailed statement about the postoperative motor status of the patient to be expected can be made intraoperatively. By way of the derivation of the D-wave, in the event of a failure of the evoked potentials derived from the muscles, it can be judged intraoperatively whether the patient will have a temporary or long-term motor deficit. This method is applied primarily in operations directly on the spinal cord, for example, of spinal cord tumors. In this case, two D-wave catheters can also be placed: one caudal (below the tumor) to monitor the relay of the potentials beyond the site into the periphery, and one cranial (above the tumor) for technical monitoring of stimulation and system and further influencing factors.

Especially in the case of tumors located very far cranially, the D-wave catheters are relatively close to the stimulation point and the response is expected within a very short time window after the stimulation (less than 10 ms). Particularly because in this case transcranial stimulation is performed using high currents, stimulation artifacts are frequently overlaid on the D-wave in the derivative. The D-wave then cannot be unambiguously identified and characterized.

With the aid of the invention, the D-wave becomes unambiguously identifiable in all cases, but above all in the case of a discharge catheter located very far cranially.

Somatosensory evoked potentials (SEP) are understood as the stimulation of a sensory nerve in the periphery and the cortical derivation of the evoked response (on the head). One special case of SEP in this case are the SEP after stimulation of the N. trigeminus. The N. trigeminus is the fifth cranial nerve, which above all supplies sensation to parts of the face. After stimulation of the N. trigeminus, for example, by means of electrical stimulation at the corner of the mouth, evoked potentials may be derived via the primary sensory cortex. Since the waves arising in this way in the derivative have to be very small, multiple responses have to be averaged. The influence of the noise in the signal is thus reduced and the signal of interest to the user stands out more clearly. Depending on the amplitude of the original signal, a differing number of averaging procedures is necessary. In the case of trigeminus SEP, an averaging number of 50 to 200 is typical. At a repetition rate of the stimulation of, for example, 2.1 Hz, the recording and analysis lasts up to 95 seconds. At the same time, the location of the derivative is also very close to the location of the stimulation in this case, so that the electrical artifact which arises due to the stimulation stands out very strongly in the derived signal and is overlaid on the actual sensory response. This method is primarily applied in neurosurgical interventions in the region of the brainstem and can make statements in this case about the intactness of the sensory part of the N. trigeminus. With the aid of the invention, the stimulation artifact in the measurement become substantially smaller and narrower, which causes the sensory response (an electrical physiological response) to stand out more from the signal. This results, on the one hand, in a simpler identification of the response in the derived signal. On the other hand, the invention can contribute to reducing the number of averaging procedures during the signal recording and thus being able to reduce the acquisition time for measurement signals.

Motor evoked potentials (MEP) can be induced by electrical stimulation of the motor cortex. This stimulation can be performed in a transcranial manner, for example. The motor response can then be derived from corresponding muscles by needle or surface electrode(s). The corticobulbar MEPs are a special case of MEPs. In this case, the signal runs via the corticobulbar path and the motor cranial nerves to the corresponding target muscles after stimulation of the motor cortex. Above all electrical physiological signals of muscles in the region of the face, the mouth, the throat, the neck, and the nape of the neck are derived in this case. Because of the proximity of stimulation and derivation locations and because of the stimulation parameters necessary for this method, the motor response is to be expected very shortly after the stimulation pulse and the stimulation artifact is very present in the derivative. For this reason, above all small motor responses are frequently concealed by pronounced stimulation artifacts. Corticobulbar MEPs are used above all during neurosurgical interventions in the region of the brainstem and can supply statements in this case about the intactness of the motor cranial nerves. The stimulation artifacts are substantially reduced by the invention. Identification of smaller and faster motor responses is thus also possible without problems.

The above statements show by way of example and as preferred variants the use of an arrangement according to the invention in the diagnostic, in particular intraoperative field.

The circuit according to the invention is preferably an H-bridge circuit (which can furthermore also have more arms and switching elements accordingly in the case of more than two power sources) and has one or preferably two (or more) power sources, which are set inactive in the case of a null current phase to save power. Such a circuit is found in DE 10 2013 010893 A1, to which reference is expressly made here. According to the present novel invention, the bridge circuit contains a capacitance connected in series to the load resistance, in particular in the form of a capacitor, and is configured in such a way that the charge supplied during a current pulse or a sequence of current pulses is only compensated for by a countercurrent after a time delay after the stimulation pulse without stimulation and discharge current via the capacitance.

Switching elements enable currents (in particular stimulation currents) to be conducted oriented via the branches of the bridge circuit and in the case of a stimulation or the discharge of the capacitor through the load resistance. The activation of the switching elements and the power sources is preferably carried out in a computer-controlled manner for this purpose, i.e., by computer-implemented programming in such a way that after one or more stimulation current pulses, the complete discharge (reverse current flow because of the discharge of the capacitance) is only enabled with a time delay in relation to the end time of a respective last stimulation current pulse.

As indicated, as a "load resistance", a patient or one or more body parts (for example, neck, arm, leg, or head), tissue, or a tissue or organ of a patient can bridge the otherwise open bridge branch during a diagnostic examination, in particular during an operation in a patient having electrodes.

"Patient" means an animal (for example, mammal) to be examined or in particular a human to be examined, who can be healthy or sick.

The at least one power source for generating a stimulation current pulse is connected to the legs of the bridge circuit in such a way that it enables an electrical current via a leg through the bridge branch and furthermore through a leg connected to the other end of the bridge branch with corresponding switch position.

The capacitive element provided in the bridge branch with the load resistance which can be introduced (introduced in function) for generating a current for the electrical charge equalization is preferably at least one capacitor connected in series to the load resistance, for example, as a ceramic capacitor, plastic film capacitor, electrolyte capacitor, variable capacitor, or furthermore supercapacitor. In preferred embodiments of the invention, the capacitor has a capacitance of 100 nF to 100 µF.

One or more stimulation current pulses can mean in particular one or up to twenty, for example, 1 to 5, stimulation current pulses (in the case of more pulses than the stimulation current pulse sequence), which can also have different phases (polarizations), with the proviso that they cannot already effectuate a complete charge equalization per se on the stimulation electrode or electrodes (and the counter electrodes thereof). Before or after a stimulation current pulse or a pulse sequence, further stimulation current pulses or pulse sequences can be initiated, which can also be equalized with a time delay, i.e., stimulation, delayed current equalization, and measurement can be carried out multiple times in succession.

In preferred variants of the invention, the pulse width (preferably predetermined by programming) of a stimulation current pulse is preferably 0.01 to 150 ms, preferably 50 to 2000 µs, in particular 200 to 1200 µs. The delay time window, in which equalization current cannot flow, preferably extends in all variants of the invention over 1 to 1000 ms, in particular over a range of 1 to 100 ms. In preferred variants of the invention, interstimulus interval (ISI, time between the stimulation pulses) pauses of 2 to 4 ms preferably lie between individual stimulation current pulses (preferably predetermined by programming). In pulse sequences, the total duration (preferably predetermined by programming) is in preferred variants of the invention 50 µs to 116 ms (for example, in the case of up to pulse width 2000 µs, ISI 4 ms, and 20 pulses), in particular 200 µs (1 pulse having PW 200 µs) to 27.2 ms (for example, in the case of up to pulse width 1200 µs, 6 pulses, ISI 4 ms), in particular 2 ms to 50 ms.

The fact that the arrangement is configured in such a way that a delay time window is maintained between one or more stimulation current pulses and a discharge of the capacitive element via one or more stimulation electrodes means programming (preferably by means of software and an integrated computer) of a control unit, which controls the switching elements, the power sources, and the flowing of electrical currents in the arrangement and is also a component of the arrangement, which either a) conducts a very weak maintenance current (in preferred embodiments having a current strength of 1 µA to 100 µA) through the bridge branch having the load resistance which can be introduced, which is multiple times less, for example, 10 000 to 200 000 times less than the stimulation current or the total of the stimulation currents, upon which a delay time window takes place, and which keeps the capacitor charged during the delay time window (for example, the stimulation current can be 100 mA and the maintenance current 4 µA), or b) by the participating switching elements (which are then closed if necessary), by way of the control unit completely suppresses any current flow during the delay time window through the bridge branch having the load resistance which can be introduced and only enables a discharge current from the capacitor by closing participating switching elements after this delay has passed.

A load resistance which can be introduced (or synonymously one which can be introduced) in the associated bridge branch is considered to be present in the bridge branch (as a component connected in series therein) in the application case on the patient (case of the measurement and the stimulation by means of stimulation current pulses).

Electrode types, as are used for the supply of the stimulation current pulse or pulses, can also be used for the measurement of the physiological signals—the physiologically occurring currents are then not derived via the bridge branch having the load resistance which can be introduced or is introduced in case of application, but rather conducted by means of the control unit via a measuring unit (integrated therein or separate) by means of one or more separate lines (which can preferably also be switched on and off)—these can be invasive or noninvasive electrodes.

In particular needle electrodes in various forms (linear, angled, corkscrew) or surface or adhesive electrodes are used as electrodes. Voltage differences are thus measured (for example, in the order of magnitude of 1 nV to 1000 mV), which arise due to physiological activity or muscle movement. These voltage differences can be derived from the surface of the body or invasively, for example, directly from a muscle.

In this manner, the physiological measurement signals (and/or the corresponding electrophysiological signals (currents), such as EMG signals, action potentials of nerves, or the like) can be obtained and derived substantially without interference. By means of a display unit and possibly a storage unit, they can then be visualized for the examining physician or surgeon, for example, as numeric values, graphic representations, or by means of a color code (for example, traffic signal having green for healthy signal, yellow for questionable signal, or red for pathological signal), and/or can be made accessible in another manner, possibly only after storage and analysis after the measurements, so that the required items of information, for example, about nerve or organ integrity or function, are available to the examining physician or surgeon for diagnostic or intraoperative measures. By means of the optional storage unit (which can be component of the arrangement), they can also be saved for later analysis.

If reference is made to one or more stimulation current pulses, this refers to a single (monophasic or biphasic) pulse or a sequence of such stimulation current pulses.

The duration of a stimulation pulse or a stimulation pulse sequence is preferably in the range of 0.01 to 150 ms, in particular in the range of 0.2 to 30 ms, in all variants of the invention.

A further embodiment of the invention relates to a method for in particular intraoperative stimulation, in which an arrangement according to the invention as defined above or hereafter is used for producing stimulation current pulses and a reaction on an effector organ, for example, a muscle twitch and/or a pressure signal or in particular an electrophysiological signal such as electromyography (EMG), or evoked potential (EP) is measured to be able to check whether a nerve connection or a brain area which is a condition for the stimulus conduction to the effector body part, tissue, or organ or the formation of the stimulation required for this purpose is intact or entirely or partially damaged.

A further embodiment relates to a method for in particular intraoperative determination of damage to a nerve connection or a brain area, in which the above method is used.

The invention also relates to the use of an arrangement according to the invention as described above or hereafter, in which it is used to produce stimulation currents which act on the patient and preferably a reaction on an effector organ, for example, a muscle twitch and/or a pressure signal or in particular an electrophysiological signal, such as electromyography (EMG) or evoked potential (EP) is measured to be able to check whether, for example, a nerve connection or a brain area which is a condition for the stimulus conduction to the effector organ or the formation of the stimulation required for this purpose is intact or entirely or partially damaged.

Preferably (in one particular embodiment variant), an arrangement according to the invention has an H-bridge circuit having four legs as a bridge circuit.

In a further preferred embodiment variant, an arrangement according to the invention described above or hereafter has as a load resistance a tissue, organ, and/or body part of a patient, which is connected in series to the bridge branch via one or more stimulation electrodes.

In a further preferred variant, an arrangement according to the invention as described above and hereafter is configured in such a way that before and/or after one or more stimulation current pulses through the bridge branch having the load resistance, the capacitive element is in series with the load resistance and is discharged after the delay time window in such a way that at least one equalization current polarized opposite to the stimulation current pulse or the sum of the stimulation current pulses is released for electrical charge equalization in the region of the load resistance, in particular of tissue or an organ of a patient.

In a further preferred variant, the capacitive element of an arrangement according to the invention as described above and hereafter is a capacitor, in particular as described above.

In a further preferred variant, an arrangement according to the invention as described above and hereafter is configured in such a way that the current flow through the load resistance is interrupted between the stimulation current pulse or pulses and the equalization current or currents.

In a further preferred variant, an arrangement according to the invention as described above and hereafter is configured in such a way that a measurement of (in particular electro-) physiological signals induced by the stimulation current pulse or pulses from the load resistance via at least one signal derivation electrode is performed at a time during the delay time window at which stimulation current and equalization current are not conducted through the load resistance.

In a further preferred variant, an arrangement according to the invention described above and hereafter is configured in such a way that to maintain the charge in the capacitive element during the delay time window before or in particular after the stimulation current pulse or pulses, a weak maintenance current is conducted through the bridge element and the load resistance, which is less (lower current strength) than the stimulation current pulse (in relation to its maximum current strength), but is oriented identically (identical polarization), and which prevents the equalization current or currents from being able to drain off from the capacitive element as long as the maintenance current flows.

In a further preferred variant, an arrangement according to the invention described above and hereafter is configured (in particular programmed) in such a way that the maintenance current is switched off as soon as the equalization current is supposed to flow.

In a further preferred variant, an arrangement according to the invention described above and hereafter is characterized in that the switching elements are actuated in such a way that due to (matching) setting of the switching elements in the stimulation-current-pulse-free delay time window before or in particular after one or more stimulation current pulses, an equalization current cannot flow through the bridge branch having the load resistance and in the current-pulse-free delay time window between equalization current or currents and stimulation current pulse or pulses, electrical signals (in particular electrophysiological signals) of the load resistance evoked by the one or the multiple stimulation current pulses are derived and measured.

In a further preferred variant, an arrangement according to the invention described above and hereafter is characterized in that the setting of the switching elements is controlled by a computer program implemented in the arrangement (in particular in a control unit).

In a further preferred variant, an arrangement according to the invention described above and hereafter is configured in such a way that the duration of a stimulation current pulse or a stimulation current pulse sequence is in the range of 0.01 to 150 ms, in particular in the range of 0.2 to 30 ms, and the delay time window in which equalization current cannot flow, extends over 1 to 1000 ms, in particular over the range of 1 to 100 ms.

In a further preferred embodiment variant, an arrangement according to the invention described above and hereafter is characterized in that at least one uniphasic power source having low idle power consumption is coupled as a power source by means of an H-bridge (according to the invention) in such a way that it is only active for the time span of a stimulation current pulse or a stimulation current pulse sequence and is only activated directly before the stimulation current pulse to save power.

In a further preferred variant, an arrangement according to the invention described above and hereafter contains two uniphasic power sources having low power consumption, which are coupled in such a way that during a stimulation time span, only one of the power sources at a time can transmit a stimulation current pulse or a stimulation pulse sequence via the load resistance.

A further preferred variant of the invention relates to a method or process for diagnostic, in particular intraoperative, electrical stimulation and measurement of resulting electrical reactions (electrophysiological reactions) in a load resistance in the form of a body or body part of a patient, in which an arrangement according to the invention described above or hereafter is used for producing at least one simulation current pulse and at least one charge equalization current, which results therefrom and is stored in a capacitive element in series circuit with the load resistance, and an electrical reaction of the load resistance is derived and measured in a delay time window without stimulation current and without charge equalization current.

A further preferred variant of the invention relates to the use of an arrangement according to the invention described above or hereafter for producing at least one stimulation current pulse and at least one charge equalization current, which results therefrom and is stored in a capacitive element in series circuit with the load resistance, wherein an electrical reaction of the load resistance is derived and measured in a delay time window without stimulation current and without charge equalization current.

Finally, in a further variant, the invention relates to the use of an arrangement according to the invention described above or hereafter for producing stimulation currents, which act on a patient and induce electrical reactions in the patient, which can be derived and measured and are used in the application.

Further preferred embodiments of the invention are found in the claims and in particular the dependent claims and in the examples, which describe special variants (embodiments) of the invention. The claims are incorporated here by reference.

DETAILED DESCRIPTION

The following example and also the figures are used to illustrate the invention, without restricting its scope. The individual exemplary features can also be used instead of more general defined features mentioned above and hereafter, individually, in multiples, or all of them, in the embodiments of the invention mentioned outside the example instead of the more general features used therein.

Identical reference signs all have identical meanings in all figures.

Figure 2:
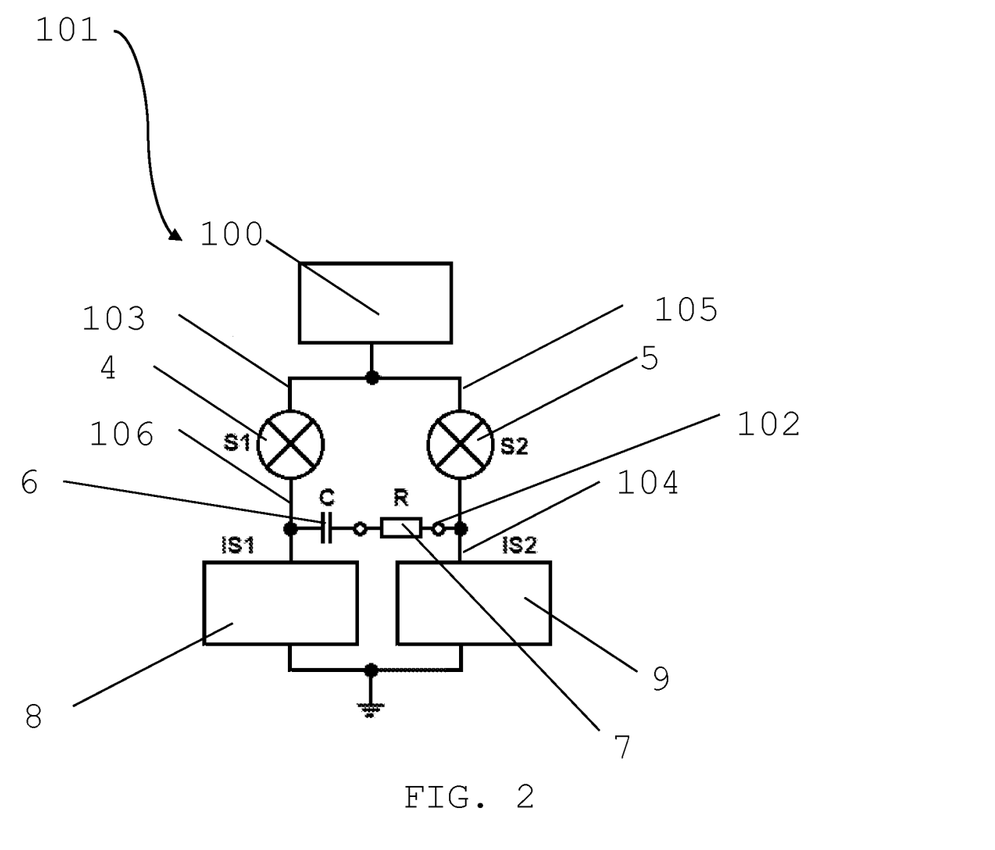
FIG. 2 shows a schematic view of an exemplary arrangement according to the invention for generating stimulation current pulses, which enables a delayed charge equalization by means of installed capacitance.
Figure 3:
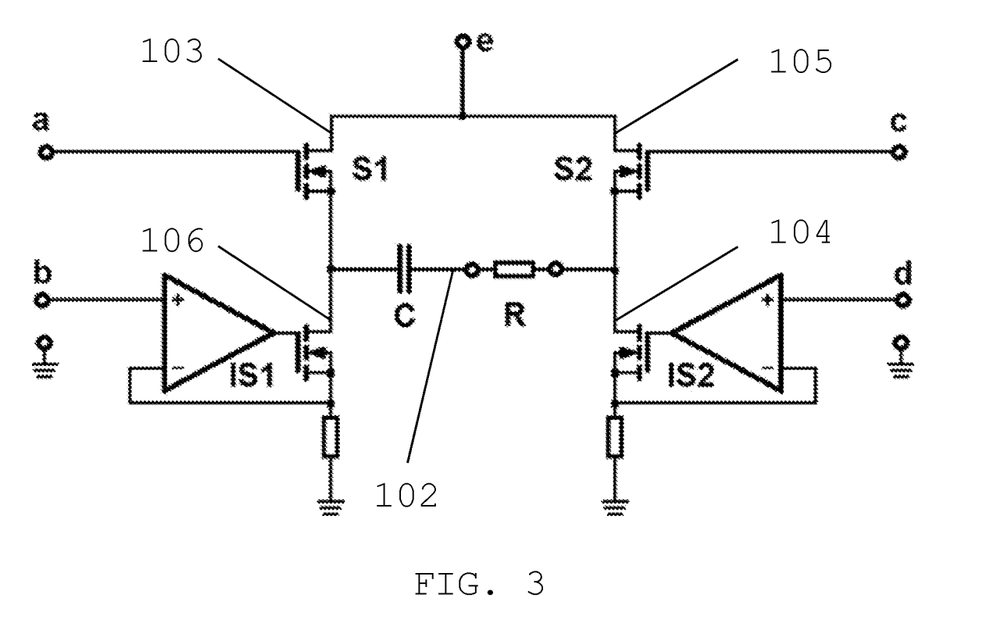
FIG. 3 shows a more detailed schematic illustration of an arrangement according to the invention for generating stimulation current pulses, which enables a delayed charge equalization by means of installed capacitance and programming, having details on switching elements and power sources.

The location of the voltage source 100 in following FIG. 2 is only to be considered to be an exemplary arrangement—instead the voltage source 100 can also, for example, be implemented at the bottom (below the node point of the legs 104 and 106 or thereon), as a component of IS1 and IS2 (as shown in FIG. 3), or as a component of S1 and S2. The voltage source can consist, for example, of a voltage (generally approximately 4.75 to approximately 5.25 V transformed) resulting from a suitable interface (i.e., enabling a sufficient base voltage) such as a USB terminal, for example, of a terminal or a power supply unit, which enables particularly simple handling.

FIG. 2 shows an arrangement according to the invention, embodied here in the form of an H-bridge circuit 101. FIG. 1 shows the current curve when, in an H-bridge circuit according to the invention having capacitor 6 (C) as shown in FIG. 2 or FIG. 3, a stimulation current pulse 1 extending via the legs 103 and 104 (or the legs 105 and 106) is conducted through the bridge branch 102. If one leaves the respective associated switching elements S1 4 and IS2 9 (or in the alternative case S2 5 and IS1 8) open after administering a stimulation current pulse 1, the capacitor 6 (C) thus discharges via the load resistance 7 (R) (for example, a patient, a body part, organ, or tissue of a patient) having current flow direction opposite to the stimulation current pulse 1 having a current curve shown idealized during charge equalization 2.

Figure 7:
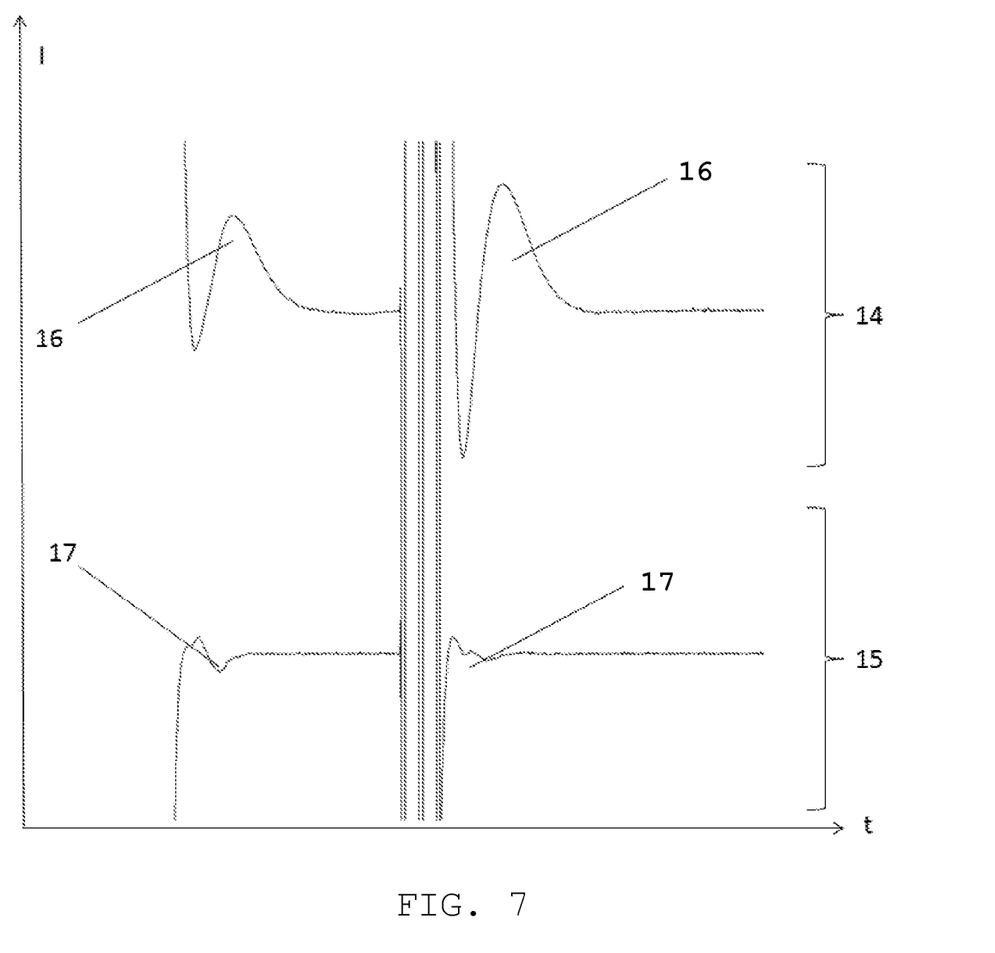
FIG. 7 graphically shows on top the electrophysiological signals (measurement signal currents) actually obtained by a stimulation current pulse sequence after a CoMEP without delayed charge equalization, and on the bottom the actually obtained electrophysiological signals (measurement signal currents) having delayed charge equalization according to the invention.

FIG. 7 shows on the basis of the example of the measurement of the signal of a CoMEP (this term is explained above), which negative consequences this has for the shape and intensity of the signal to be measured: The curve 14 shows a CoMEP without delayed charge equalization—the discharge current directly follows the stimulation current pulses 18 here (only shown partially in the middle of the figure) and a strong distortion of the signals to be measured occurs. The substantially smaller response signal is overlaid thereby.

The situation represented in a first variant is very different if, according to the invention, the switching elements, the legs 103 and 104 (or in the alternative case the legs 105 and 106) no longer enable a current flow via the bridge branch 102 after the stimulation pulse 1, for example, by closing the respective associated switching elements S1 4 and IS2 9 (or in the alternative case S2 5 and IS1 8).

Alternatively, in a second variant a weak current (for example, of 4 µA) can be conducted through the capacitor to maintain the charge of the capacitor, so that it cannot discharge.

The control of both variants is performed by a (correspondingly) programmed control unit (not shown), which implements the opening and closing of the switching elements in the first variant and implements the maintenance of the weak current in the second variant, respectively.

However, if one waited too long, processes at the stimulation electrode or electrodes on the patient as the load resistance R after a stimulation current pulse 1 would be reversible too little. Therefore after a short delay time window (for example, of 100 ms duration), during which the electrical physiological signal to be measured can be measured, the flow of the discharge current out of the capacitor 6 is enabled.

Figure 4:
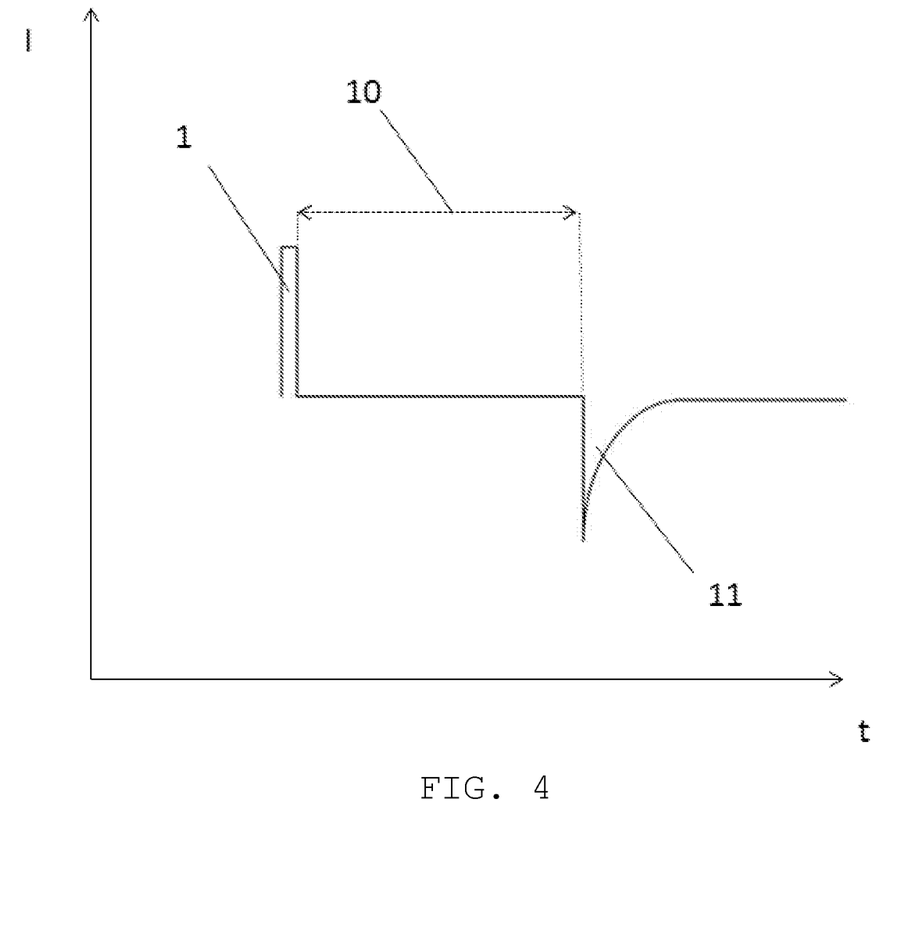
FIG. 4 graphically shows the idealized current curve of a monopolar stimulation current pulse having delayed charge equalization according to the invention (without the electrophysiological reaction).

FIG. 4 shows the current curve thus resulting (without physiological signal) in an arrangement according to the invention: After the stimulation current pulse 1, during a delay time (delay time window) 10, the discharge of the capacitor 6 is prevented, in the first variant by closing switches, in the second variant by the weak current (not shown in the drawing) for maintaining the charge of the capacitor 6. The discharge of the capacitor 6 via the load resistance 7 in the bridge branch 102 is only enabled after passage of the delay time 10, in the first variant by opening the respective required switching elements or in the second variant by shutting off the weak current for the charge maintenance, so that a current flows which opposes the stimulation current pulse. FIG. 4 shows the idealized current curve with delayed charge equalization (see current curve upon discharge of the capacitor 11).

Figure 5:
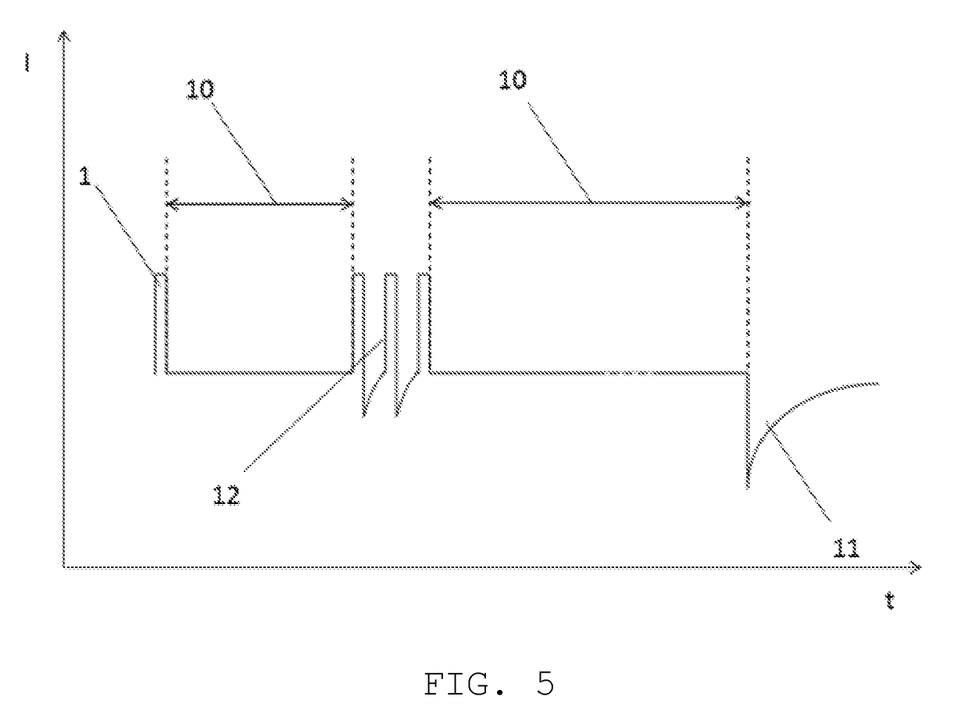
FIG. 5 graphically shows the idealized current curve of an exemplary current pulse sequence having (substantially) delayed charge equalization.

FIG. 5 shows a situation in which not only a stimulation current pulse 1 is supplied, but rather subsequently a sequence of (by way of example three here) stimulation current pulses is subsequently administered as the stimulation current pulse sequence 12. After the stimulation current pulse 1, a first delay time 10 for the discharge of the capacitor 6 is inserted until the beginning of the stimulation current pulse sequence 12, during which no discharge takes place. During the stimulation current pulse sequence 12, after each individual stimulation current pulse constituting it, the capacitor is partially discharged (downwardly oriented current indication in FIG. 5 having opposing polarization), but at the end of the stimulation current pulse sequence 12, during a further delay time 10, the discharge of the capacitor is suppressed (by means of one of the two above-described variants). The discharge of the capacitor 6 can thus only take place after passage of the delay time 10, which results in the current curve shown idealized as 11 upon discharge of the capacitor.

Figure 6:
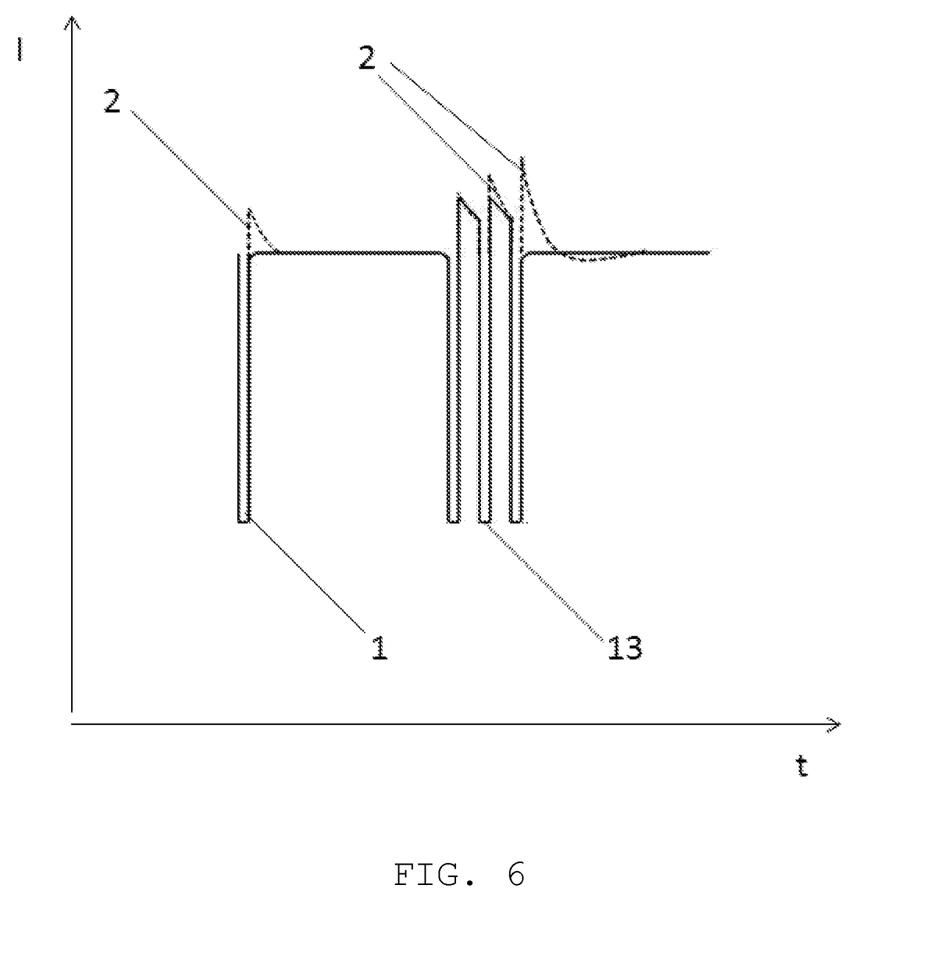
FIG. 6 graphically shows in idealized form a direct comparison of the current curve of a stimulation pulse sequence with (solid line) and without (dashed line) delayed charge equalization according to the invention.

The currents are shown in FIG. 6 after a stimulation current pulse 1 (with inverted polarity in relation to the previous stimulation current pulses here) and a stimulation current pulse sequence 13 once without the delay carried out according to the invention of the discharge (dashed lines and part of the solid line which is not replaced by the dashed line) and with implemented delay of the discharge (entire solid line). 2 is the current curve with charge equalization (left partially, very right completely).

Finally, the top of FIG. 7 in the region 14 shows the results measured during a CoMEP experiment, which is measured without delay of the charge equalization (curve 16, where charge equalization and measured response are overlaid) and the bottom in the region 15 shows the corresponding situation with delay of the charge equalization, where the curve sections 17 display the weak measurement signals which are hardly still impaired. The charge equalization takes place here in the illustrated region which is not visible.

An arrangement according to the invention equipped with means for delaying a discharge of the capacitor 6 thus enables much more accurate measurements of the physiological electrical reactions to stimulation current pulses than would be possible with direct discharge, and it is thus made at all reasonable for the first time to use a capacitor in the bridge branch 102 to reduce artifacts induced by stimulation currents because of electrolytic and other procedures during stimulation and measurement on the patient by charge equalization.

LIST OF REFERENCE NUMERALS

| Reference numeral | Meaning |
|---|---|
| 1 | stimulation current pulse |
| 2 | current curve upon charge equalization |
| 3 | (not assigned) |
| 4 | switching element S1 |
| 5 | switching element S2 |
| 6 | capacitor |
| 7 | load resistance |
| 8 | switching element IS1 |
| 9 | switching element IS2 |
| 10 | delay time |
| 11 | current curve upon discharge of the capacitor |
| 12 | stimulation current pulse sequence |
| 13 | stimulation current pulse sequence |
| 14 | CoMEP without delayed charge equalization |
| 15 | CoMEP with delay of the charge equalization |
| 16 | charge equalization without delay |
| 17 | measurement signals |
| 18 | stimulation current pulse |
| 100 | voltage source |
| 101 | H-bridge circuit |
| 102 | bridge branch |
| 103 | leg |
| 104 | leg |
| 105 | leg |
| 106 | leg |

The invention claimed is:

1. An arrangement, configured for electrical charge equalization after generation of one or more stimulation current pulses, the arrangement comprising:
a bridge circuit,
switching elements,
a bridge branch between two legs of the bridge circuit, into which a load resistance is introducible,
at least one power source for generating at least one stimulation current pulse, which is connected to the legs of the bridge circuit in such a way that the at least one power source enables an electrical current via one leg through the bridge branch and through a leg connected to the other end of the bridge branch at a matching switch position,
a capacitive element in the bridge branch, the capacitive element being configured solely for generating a current for electrical charge equalization of current introduced by one or more stimulation current pulses, and the arrangement is configured in such a way that, between one or more stimulation current pulses and a discharge of the capacitive element solely for the electrical charge equalization via one or more stimulation electrodes, a delay time window is maintained, which is used for measuring electrical physiological signals induced as a reaction to the stimulation current pulse or pulses, wherein the arrangement is further configured in such a way that a measurement of physiological signals induced by the stimulation current pulse or pulses into the load resistance is performed via at least one signal derivation electrode at a location different from a stimulation site of the two legs of the bridge circuit where the at least one stimulation current pulse is introduced into the load resistance at a point in time during the delay time window at which no stimulation current and no equalization current are conducted through the load resistance.

2. The arrangement as claimed in claim 1, wherein the bridge circuit is an H-bridge circuit having four legs.

3. The arrangement as claimed in claim 1, wherein the load resistance is adapted to be at least one of a tissue, organ, or body part of a patient, which is connected in series via one or more stimulation electrodes to the bridge branch.

4. The arrangement as claimed in claim 1, wherein the arrangement is further configured in such a way that at least one of before or after one or more stimulation current pulses through the bridge branch having the load resistance, the capacitive element, which is in series with the load resistance, is discharged after the delay time window in such a way that at least one equalization current polarized opposite to the stimulation current pulse or a sum of the stimulation current pulses is released for electrical charge equalization in a region of the load resistance.

5. The arrangement as claimed in claim 4, wherein the capacitive element is a capacitor.

6. The arrangement as claimed in claim 1, wherein the arrangement is further configured in such a way that a current flow through the load resistance is interrupted between the stimulation current pulse or pulses and the equalization current or currents.

7. The arrangement as claimed in claim 1, wherein the arrangement is further configured in such a way that to maintain a charge in the capacitive element during the delay time window, before or after the stimulation current pulse or pulses, a weak maintenance current is conducted through the bridge element and the load resistance, which is less than the stimulation current but has a same orientation, and which prevents the equalization current or currents from being able to drain out of the capacitive element as long as the maintenance current flows.

8. The arrangement as claimed in claim 7, wherein the arrangement is further configured in such a way that the maintenance current is shut down as soon the equalization current is supposed to flow.

9. The arrangement as claimed in claim 1, wherein the switching elements are actuated in such a way that by corresponding setting of the switching elements, in a stimulation-current-pulse-free delay time window before or after one or more stimulation current pulses, the equalization current cannot flow through the bridge branch having the load resistance and, in the current-pulse-free delay time window between the equalization current or currents and the stimulation current pulse or pulses, electrical signals of the load resistance evoked by one or more stimulation current pulses are derived and measured.

10. The arrangement as claimed in claim 9, wherein the setting of the switching elements is controlled by a computer program implemented in the arrangement.

11. The arrangement as claimed in claim 1, wherein the arrangement is further configured in such a way that the duration of a stimulation current pulse or a stimulation current pulse sequence is in the range of 0.01 to 100 ms, and the delay time window, in which no equalization current can flow, extends over 1 to 1000 ms.

12. The arrangement as claimed in claim 1, wherein at least one uniphasic power source, having low idle power consumption, is coupled as a power source by an H-bridge in such a way that it is only active for the time span of a stimulation current pulse or a stimulation pulse sequence and that is only activated directly before the stimulation current pulse or pulses to save power.

13. The arrangement as claimed in claim 12, wherein the at least one uniphasic power source comprises two uniphasic power sources having low power consumption, which are coupled in such a way that during a stimulation time span, only one of the power sources at a time can emit a stimulation current pulse or a stimulation pulse sequence via the load resistance.

14. A method or process for intraoperative electrical stimulation and measurement of resulting electrical reactions in a body or body part of a patient, the method comprising:

using the arrangement as claimed in claim 1 during surgery to produce at least one stimulation current pulse and at least one charge equalization current, which results from said pulse and is stored in a capacitive element in series circuit with the load resistance, and in a delay time window without stimulation current and without charge equalization current, deriving and measuring an electrical reaction using a signal derivation electrode at a location different from the stimulation site of the two legs of the bridge circuit where the at least one stimulation current pulse is introduced into the load resistance.

* * * * *